(12) United States Patent
Jackson et al.

(10) Patent No.: US 10,132,306 B2
(45) Date of Patent: Nov. 20, 2018

(54) METHOD OF GENERATING A GRADIENT FLOW HAVING A CONSTANT COMPOSITIONAL NOISE CHARACTERISTIC

(71) Applicant: Waters Technologies Corporation, Milford, MA (US)

(72) Inventors: Michael R. Jackson, Woonsocket, RI (US); Christopher Seith, Franklin, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 296 days.

(21) Appl. No.: 14/612,542

(22) Filed: Feb. 3, 2015

(65) Prior Publication Data

US 2015/0219091 A1 Aug. 6, 2015

Related U.S. Application Data

(60) Provisional application No. 61/936,395, filed on Feb. 6, 2014.

(51) Int. Cl.
*F04B 49/06* (2006.01)
*F04B 13/02* (2006.01)
(Continued)

(52) U.S. Cl.
CPC ............ *F04B 49/065* (2013.01); *F04B 13/02* (2013.01); *F04B 23/06* (2013.01); *F04B 49/06* (2013.01);
(Continued)

(58) Field of Classification Search
USPC ........................................................ 700/282
See application file for complete search history.

(56) References Cited

U.S. PATENT DOCUMENTS 3,981,620 A 9/1976 Abrahams et al.
2011/0132463 A1* 6/2011 Witt .................... F04B 11/0058
137/1

(Continued)

FOREIGN PATENT DOCUMENTS

JP S60190859 A 9/1985

OTHER PUBLICATIONS

Combined Search and Examination Report in related United Kingdom Patent Application No. GB1500997.0, dated Jul. 14, 2015; 6 pages.

*Primary Examiner* — Emilio J Saavedra
(74) *Attorney, Agent, or Firm* — Schmeiser, Olsen & Watts LLP; William G. Goerin

(57) ABSTRACT

Described is a method of generating a flow having a composition gradient. A plurality of pump strokes is generated for each pump in a plurality of pumps. Each pump stroke has an initiation time and provides a volume contribution of a liquid to be mixed in the flow according to the composition gradient for the flow. The pump strokes of the pumps are controlled so that a sum of the volume contributions of the liquids that occurs between consecutive initiations of one of the pumps is maintained at a constant value throughout the duration of the flow. For each pump, the flow rates and the times between stroke initiations can change as long as the sum of all volumes contributed between the consecutive initiations of one of the pumps is held constant. Advantageously, the method achieves a constant compositional noise characteristic throughout the duration of the flow.

9 Claims, 3 Drawing Sheets

(51) Int. Cl.
*F04B 23/06* (2006.01)
*F04B 49/12* (2006.01)
*F04B 49/20* (2006.01)
*G01N 30/34* (2006.01)

(52) U.S. Cl.
CPC .............. *F04B 49/12* (2013.01); *F04B 49/20* (2013.01); *G01N 30/34* (2013.01)

(56) References Cited

U.S. PATENT DOCUMENTS

2011/0261642 A1* 10/2011 Shreve .................. G01N 30/34
366/152.2
2012/0205314 A1* 8/2012 Davison ................ G01N 30/34
210/656

\* cited by examiner

METHOD OF GENERATING A GRADIENT FLOW HAVING A CONSTANT COMPOSITIONAL NOISE CHARACTERISTIC

RELATED APPLICATION

This application claims the benefit of the earlier filing date of U.S. Provisional Patent Application Ser. No. 61/936,395, filed Feb. 6, 2014 and titled "Method of Generating a Gradient Flow Having a Constant Compositional Noise Characteristic," the entirety of which is incorporated herein by reference.

FIELD OF THE INVENTION

The invention relates generally to high pressure gradient formation liquid chromatography. More particularly, the invention relates to a method for high pressure gradient formation based on controlling the pump strokes of solvent pumps to manage compositional noise in a mobile phase gradient.

BACKGROUND

In high pressure gradient liquid chromatography, the contributions of two or more solvents to the mobile phase change over time. Generally, pumping systems for high pressure gradient liquid chromatography utilize parallel pumps to deliver multiple liquids in defined proportions to achieve a time-dependent mobile phase composition. Typically, each pump in the system is a combination of individual pump heads that are periodically refilled to maintain a constant fluid flow. The refilling of pump heads can cause disturbances in the flow, pressure and liquid composition delivered by the pumping system. The result can be compositional noise which can be problematic, for example, by causing deviation from the desired gradient composition. In addition, the compositional noise typically has a frequency characteristic that changes during the time the gradient is performed.

SUMMARY

In one aspect, a method of generating a flow having a composition gradient includes generating a plurality of pump strokes with a first pump. Each of the pump strokes of the first pump has an initiation time and provides a volume contribution of a first liquid to the flow. The volume contributions of the first pump change in time based on a contribution of the first liquid to the flow according to a predetermined composition gradient. The method also includes generating a plurality of pump strokes with at least one additional pump. Each of the pump strokes of each of the additional pumps provides a volume contribution of an additional liquid to the flow. The volume contributions of each of the additional pumps change in time based on a contribution of a respective one of the additional liquids to the flow according to the predetermined composition gradient. The pump strokes of the first pump and the additional pumps are controlled so that a sum of the volume contribution of the first liquid occurring between consecutive initiations of the first pump and volumes of the additional liquids contributed by the additional pumps between the consecutive initiations of the first pump is constant throughout a duration of the predetermined composition gradient.

In another aspect, a pump system includes a first pump, at least one additional pump and a processor in communication with the first pump and additional pumps. The first pump is operable to generate a plurality of pump strokes. Each pump stroke of the first pump has an initiation time and provides a volume contribution of a first liquid to a flow. The volume contributions of the first pump change in time based on a contribution of the first liquid to the flow according to a predetermined composition gradient. The additional pumps are operable to generate a plurality of pump strokes. Each of the pump strokes of each of the additional pumps provides a volume contribution of an additional liquid to the flow. The volume contributions of each of the additional pumps change in time based on a contribution of a respective one of the additional liquids to the flow according to the predetermined composition gradient. The processor is configured to control the pump strokes of the first pump and the additional pumps so that a sum of the volume contribution of the first liquid between consecutive initiations of the first pump and volumes of the additional liquids contributed by the additional pumps between the consecutive initiations of the first pump is constant throughout a duration of the predetermined composition gradient.

In yet another aspect, a computer program product for generating a flow having a composition gradient includes a computer readable storage medium having computer readable program code embodied therewith. The computer readable program code includes computer readable program code configured to generate a plurality of pump strokes with a first pump. Each of the pump strokes of the first pump has an initiation time and provides a volume contribution of a first liquid to a flow. The volume contributions of the first pump change in time based on a contribution of the first liquid to the flow according to a predetermined composition gradient. The computer readable program code also includes computer readable program code configured to generate a plurality of pump strokes with at least one additional pump. Each of the pump strokes of each of the additional pumps provides a volume contribution of an additional liquid to the flow. The volume contributions of each of the additional pumps change in time based on a contribution of a respective one of the additional liquids to the flow according to the predetermined composition gradient. The computer readable program code further includes computer readable program code configured to control the pump strokes of the first pump and the additional pumps so that a sum of the volume contribution of the first liquid occurring between consecutive initiations of the first pump and volumes of the additional liquids contributed by the additional pumps between the consecutive initiations of the first pump is constant throughout a duration of the predetermined composition gradient.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Figure 1:
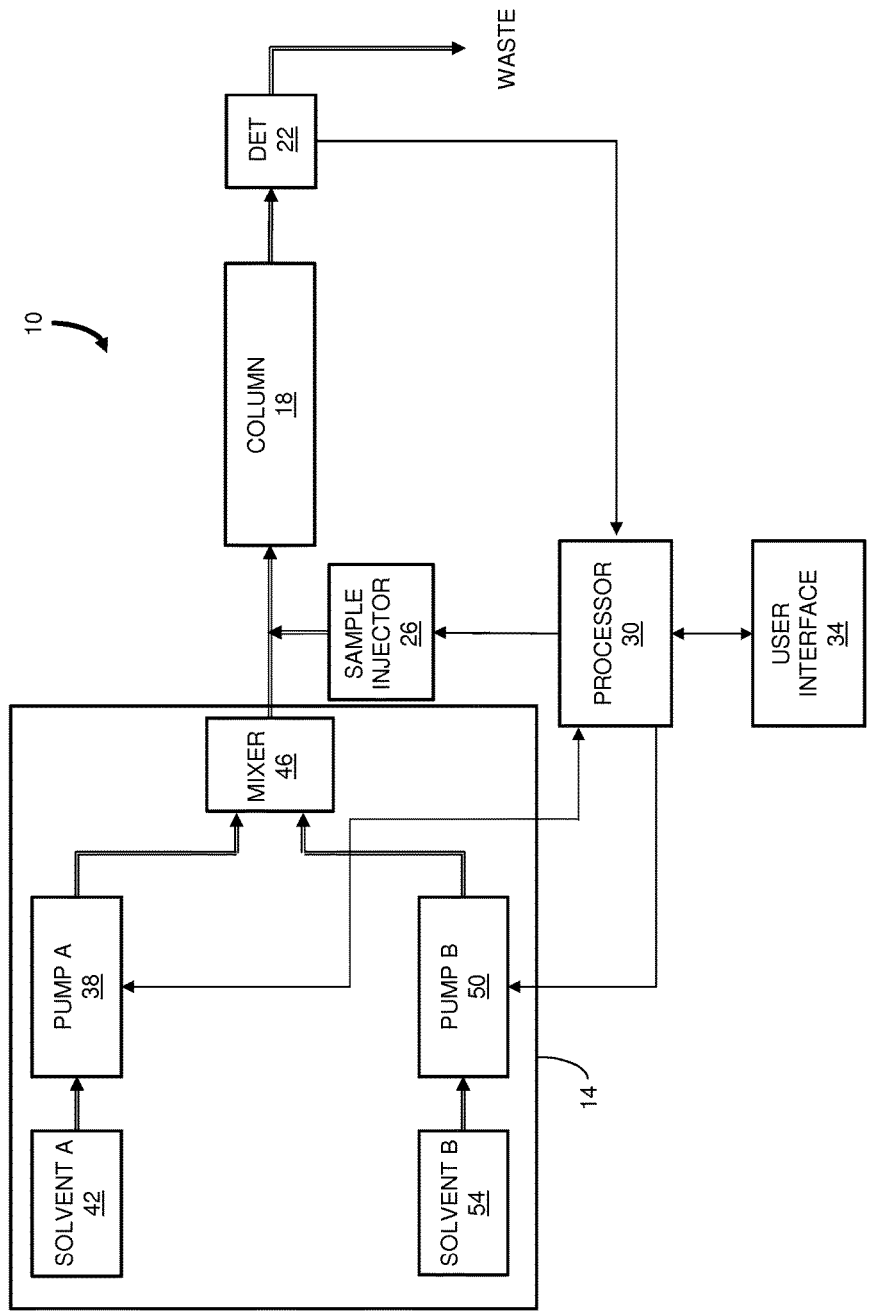
FIG. 1 is a block diagram of a liquid chromatography system that includes a binary solvent delivery system.

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

As used herein, the phrase "pump stroke displacement" should be understood to be the displacement volume of a pump head during a pump stroke and "volume contribution" should be understood to be the volume of a liquid transferred from the pump head during a pump stroke. The volume contribution may be different from the pump stroke displacement due to a variety of factors, such as liquid compressibility and hydraulic inertia.

In brief overview, the invention relates to a method of generating a flow having a composition gradient. Pump strokes are generated by at least two pumps. Each pump stroke of a pump has an initiation time and provides a volume contribution of a liquid to the flow. The volume contributions can change over time according to the required contribution of the each liquid to the predetermined composition gradient. The pump strokes of each pump are controlled throughout the composition gradient so that the sum of the volumes of liquids contributed by all of the pumps between consecutive initiation times of one of the pumps is constant regardless of time. Thus, the flow rate of the combined liquids is not relevant; however, the total volumetric frequency, measured from initiation of a pump stroke of one of the pumps to the initiation of the immediately following pump stroke of that pump, remains constant. Stated otherwise, the system of multiple pumps delivers a fixed combined volume between the two consecutive initiations of the pump, regardless of the volumes delivered individually by each pump. In addition, the flow rate of the combined liquids can change and the time between stroke initiations can change as long as the sum of the volumes contributed between consecutive initiations of one of the pumps does not change.

By way of an example, the liquids may be chromatography solvents and the flow may be a mobile phase gradient used to perform liquid chromatography. Advantageously, the size and design of a mixer downstream from the pumps can be based on the constant compositional noise. If the compositional noise frequency is established at a sufficiently high value, a smaller mixer can be employed and may more effectively address the compositional noise. More generally, the method requires no special relationship between the pump stroke volumes of the pumps to achieve the constant compositional noise if there is no requirement to meet the compositional definition of a gradient as long as the combined volumetric frequency of the refilling of the pump heads remains fixed through the duration of the composition gradient.

The present teaching will now be described in more detail with reference to embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

A block diagram of a liquid chromatography system 10 is shown in FIG. 1 and includes a binary solvent delivery system 14 coupled to the inlet of a chromatographic column 18. The outlet of the column 18 is coupled to a detector 22. An injector valve 26 introduces a sample containing one or more sample components into the mobile phase provided by the binary solvent delivery system 14. The sample components adsorb to the stationary phase inside the column 18 to varying degrees. Components with a strong attraction to the stationary phase move more slowly through the column 18 than components with a weak attraction. Thus the components are separated according to the different speeds of movement through the column 18 and elute at different times. The component with the least affinity for the stationary phase elutes first, while the component with the greatest affinity for the stationary phase elutes last. The detector 22 analyzes the emerging stream by measuring a property that is related to the concentration and characteristic of chemical composition. By way of specific examples, the measured property can be refractive index or ultra-violet absorption.

A processor module 30 controls the operation of the binary solvent delivery system 14, sample injector 26 and detector 22. The processor module 30 can include one or more processing units and memory units, and may coordinate operational and control signals used to operate other components and subsystems of the liquid chromatography system 10. A user interface 34 in communication with the processor module 30 allows for various parameters of a chromatographic measurement to be defined and for output and display of operational and measurement data to a user.

In the illustrated binary solvent delivery system 14, a first pump 38 draws a first solvent A from a reservoir 42 and supplies the first solvent at a desired flow rate and pressure to a mixer 46. A second pump 50 draws a second solvent B from a second reservoir 54 and supplies the second solvent at a desired flow rate and pressure to the mixer 46. The solvents are blended at the mixer 46 to achieve a solvent mixture having desired mobile phase properties. The flow rate of each solvent can be adjusted to vary the composition of the solvent mixture over time. A variation in the solvent mixture over time is referred to as a solvent gradient or compositional gradient.

Solvent pumps can be configured in a variety of ways. By way of a particular example, each solvent pump can be configured with two pump heads in a serial arrangement. Typically, one of the pump heads has a larger displacement volume and functions as a primary pump, and the other pump head has a smaller displacement volume and functions as an accumulator pump. The pump strokes of the primary and accumulator pumps operate with opposite phase. In an alternative configuration, pump heads are configured in a parallel arrangement with each pump head operating in opposite phase from the other pump head. One pump head delivers solvent while the other pump head is refilled with solvent.

During a conventional gradient liquid chromatography process, the relative contributions of the two solvents A and B to the mobile phase change in time. Typically, the contribution of a solvent is defined through the control of the flow rate of the corresponding solvent pump. Each pump stroke provides a volume contribution of the solvent based on the displacement volume of the pump head during the pump stroke. The pump stroke volume may be different from the displacement volume of the pump head due to the compressibility of the solvent. Typically, a flow rate of a solvent pump is increased by increasing the pump stroke frequency of the solvent pump while maintaining a constant pump stroke displacement. Conversely, the flow rate of a solvent pump is decreased by decreasing the pump stroke frequency of the solvent pump while the pump stroke displacement remains constant. The pump stroke frequencies of the two pumps are changed in a complementary manner throughout the liquid chromatography process so that the total solvent flow rate remains constant.

The durations of the pump strokes change according to changes in the pump stroke frequency for the pump. One pump has increasing pump stroke durations while the other pump has decreasing pump stroke durations. Consequently, the times when pump strokes are initiated for one pump are not fixed relative to the times when the pump strokes are initiated for the other pump. Moreover, the compositional noise characteristics due, at least in part, to the fluctuations of the flow rate of each pump changes in time because the initiation of pump strokes for the two pumps are not fixed relative to each other. Thus the frequency characteristic of the compositional noise for the solvent delivery system changes throughout the gradient liquid chromatography process.

According to an embodiment of a method of generating a flow having a gradient composition, a number of pumps provide volume contributions of a liquid to a flow which is a mixture of the liquids. Each volume contribution of a liquid is the result of a pump stroke of the respective pump. Each pump stroke has an initiation time. The initiation times of pump strokes for each pump are not necessarily correlated with the initiation times of the pump strokes of any of the other pumps. The volume contributions of the pumps may change in time according to a predetermined composition gradient. For example, the liquids may be chromatography solvents and the composition gradient may be used to perform a chromatographic analysis.

Figure 2:
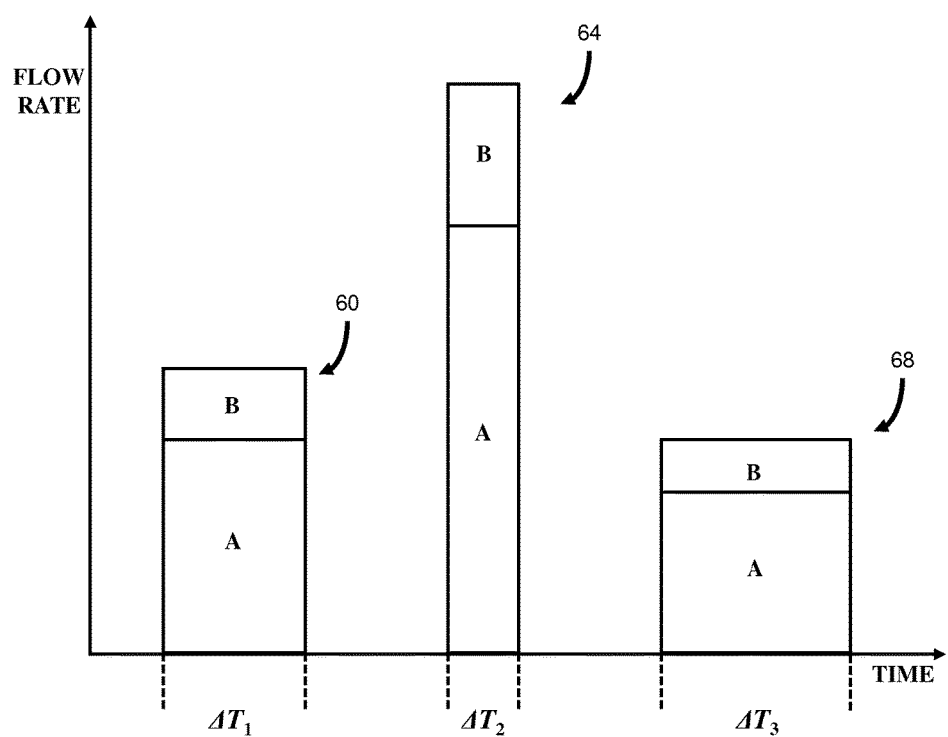
FIG. 2 shows three graphical representations of the volume contributions for pump strokes for the solvent pumps of FIG. 1 according to one embodiment.

The method includes controlling the pump strokes so that a sum of the volumes of all the liquids contributed between the times of consecutive initiations of one of the pumps is held constant. By way of examples, FIG. 2 shows three different graphical representations of the volume contributions for pump strokes for the solvent pumps A 38 and B 50 of FIG. 1. Each volume contribution is shown as a rectangle. The height of each rectangle is proportional to the flow rate from the respective pump. The width of each rectangle is equal to the time between consecutive initiations of solvent pump A. Consequently, the area of each rectangle is proportional to the volume contribution of the solvent contributed during the time between consecutive initiations of pump strokes for solvent pump A. As the pump strokes of the two solvent pumps 38 and 50 are generally initiated at different times (not shown), the volume contributions of solvent B generally includes portions of the volume contributions from two consecutive pump strokes of solvent pump B 50.

Three different "volume packets" are shown. With reference to the first volume packet 60, the time between the consecutive initiations of solvent pump A is $\Delta T_1$. The second volume packet 64 shows an example where the pump stroke frequencies of the solvent pumps 38 and 50 are doubled and therefore the time between consecutive initiations of pump strokes for solvent pump A 38 is halved. To maintain a constant sum of the volume contributions, the flow rates of the pumps 38 and 50 are doubled so that the volume contributions of all the solvents during the period $\Delta T_2$ is equal to the volume contributions for volume packet 60 during the period $\Delta T_1$. The third volume packet 68 is an example where the pump stroke frequencies of the solvent pumps 38 and 50 are halved relative to the first volume packet 60 so that the volume contributions of the two solvents during the period $\Delta T_3$ is equal to the sum of the volume contributions for volume packet 60 and is also equal to the sum of the volume contributions for volume packet 64. Thus the solvent pumps 38 and 50 can be operated to provide volume packet 60, then volume packet 64 and then volume packet 68 while maintaining a constant sum of the volume contributions in each packet so that the compositional noise frequency characteristic does not change.

Figure 3:
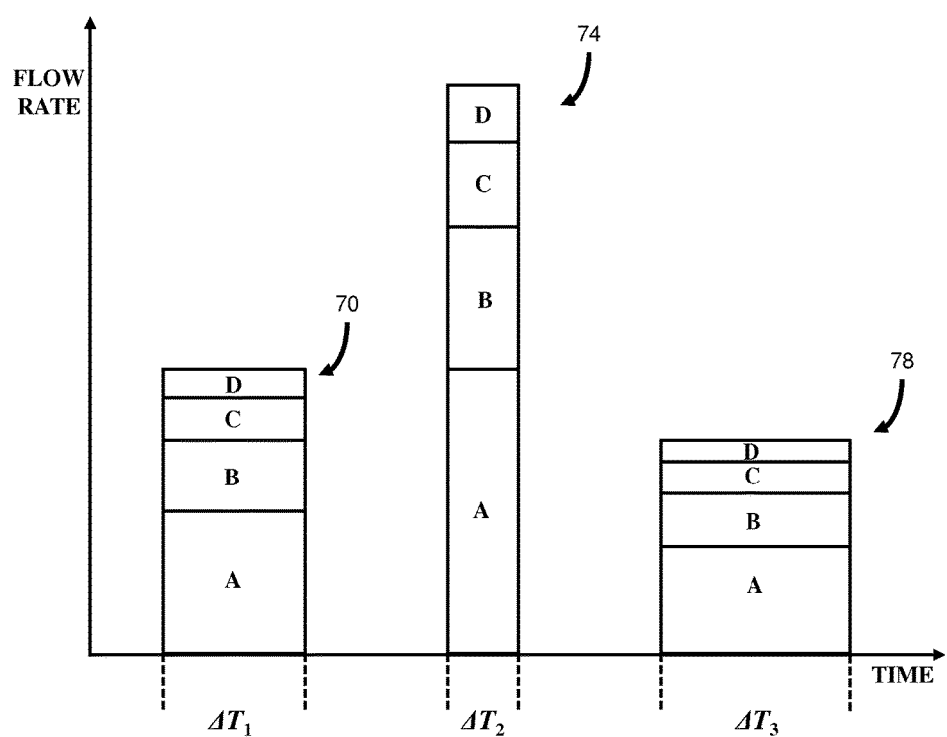
FIG. 3 shows three graphical representations of volume contributions for pump strokes for a solvent delivery system utilizing four solvent pumps according to another embodiment.

FIG. 3 shows three graphical representations of the volume contributions for pump strokes for a system having four solvent pumps designated A through D in a format similar to that of FIG. 2 and in accordance with another embodiment. For each volume packet 70, 74 or 78, the sum of the volumes of all the solvents A, B, C and D that are contributed between the times of consecutive initiations of solvent pump A is held constant.

It should be emphasized that the pump stroke frequencies of the pumps need not be related as long as the sum of the volume contributions during the volume packet, as defined by consecutive initiations of pump strokes by one of the pumps, remains constant. In one example, the initiation times of each pump are be controlled with respect to the initiation times of the other pumps to that the initiation times are interspersed in time to avoid a situation where any two pumps would otherwise initiate strokes at nearly the same time and thereby result in a deviation from a predetermined composition gradient.

Maintenance of a constant sum of the volume contributions in accordance with the various embodiments results in a constant compositional noise frequency. Advantageously, the size and design of the mixer 46 (see FIG. 1) can be based on the constant compositional noise. If the compositional noise frequency is established at a sufficiently high value, a smaller mixer can be employed and may more effectively address the compositional noise. More generally, the method requires no special relationship between the pump stroke volumes to achieve the constant compositional noise if there is no requirement to meet the requirements of a composition gradient.

While the invention has been shown and described with reference to specific embodiments, it should be understood by those skilled in the art that various changes in form and detail may be made therein without departing from the spirit and scope of the invention as recited in the accompanying claims.

What is claimed is:

1. A method of generating a flow having a composition gradient, the method comprising:
    generating a plurality of pump strokes with a first pump, each of the pump strokes of the first pump having an initiation time and providing a volume contribution of a first liquid to a flow according to a displacement volume of the pump stroke, the displacement volume and respective volume contributions of the first pump changing in time based on a contribution of the first liquid to the flow according to a predetermined composition gradient;

and generating a plurality of pump strokes with at least one additional pump, each of the pump strokes of each of the additional pumps providing a volume contribution of an additional liquid to the flow according to a displacement volume of the pump stroke of the additional pump, wherein each of the first pump and the additional pumps initiates pump strokes at a pump stroke frequency, the displacement volume and respective volume contributions of each of the additional pumps changing in time based on a contribution of a respective one of the additional liquids to the flow according to the predetermined composition gradient, the pump strokes of the first pump and the pump strokes of the additional pumps being controlled so that a sum of the volume contribution of the first liquid occurring during a time between consecutive initiations of the first pump strokes plus the volumes of the additional liquids contributed by the additional pumps during the time between the consecutive initiations of the pump strokes of the first pump is constant throughout a duration of the predetermined composition gradient.

2. The method of claim 1 wherein the pump stroke frequencies of the first pump and the additional pumps are constant throughout a duration of the predetermined composition gradient.

3. The method of claim 1 wherein the pump stroke frequency of at least one of the first pump and the additional pumps changes in time during the predetermined composition gradient.

4. The method of claim 1 wherein pump strokes of the first pump and the additional pumps have a same pump stroke frequency and the initiations of the pump strokes of the first pump and the additional pumps are interspersed in time.

5. The method of claim 1 wherein the first and second liquids are solvents to be mixed as components of a mobile phase for liquid chromatography.

6. A pump system, comprising:
a first pump operable to generate a plurality of pump strokes, each of the pump strokes of the first pump having an initiation time and providing a volume contribution of a first liquid to a flow according to a displacement volume of the pump stroke;
at least one additional pump operable to generate a plurality of pump strokes, each of the pump strokes of each of the additional pumps providing a volume contribution of an additional liquid to the flow according to a displacement volume of the pump stroke of the additional pump;
and a processor in communication with the first pump and the additional pumps, the processor configured to control the pump strokes of the first pump so that the displacement volume and respective volume contributions of the first pump change in time based on a contribution of the first liquid to the flow according to a predetermined composition gradient and configured to control the pump strokes of the additional pumps so that the displacement volume and respective volume contributions of each of the additional pumps change in time based on a contribution of a respective one of the additional liquids to the flow according to the predetermined composition gradient, the processor further configured to control the pump strokes of the first pump and the pump strokes of the additional pumps so that a sum of the volume contribution of the first liquid during a time between consecutive initiations of the first pump strokes plus the volumes of the additional liquids contributed by the additional pumps during the time between the consecutive initiations of the pump strokes of the first pump is constant throughout a duration of the predetermined composition gradient.

7. The pump system of claim 6 wherein the first pump and the at least one additional pump are solvent pumps used to provide solvents to be mixed as components of a mobile phase for liquid chromatography.

8. The pump system of claim 7 further comprising a mixer having a plurality of inlets each in fluidic communication with one of the first pump and the additional pumps, and having an outlet to provide the mobile phase.

9. A computer program product for generating a flow having a composition gradient, comprising:
a non-transitory computer readable storage medium having computer readable program code embodied therewith, the computer readable program code comprising: computer readable program code configured to generate a plurality of pump strokes with a first pump, each of the pump strokes of the first pump having an initiation time and providing a volume contribution of a first liquid to a flow according to a displacement volume of the pump stroke, the displacement volume and respective volume contributions of the first pump changing in time based on a contribution of the first liquid to the flow according to a predetermined composition gradient; computer readable program code configured to generate a plurality of pump strokes with at least one additional pump, each of the pump strokes of each of the additional pumps providing a volume contribution of an additional liquid to the flow according to a displacement volume of the pump stroke of the additional pump, the displacement volume and respective volume contributions of each of the additional pumps changing in time based on a contribution of a respective one of the additional liquids to the flow according to the predetermined composition gradient; and computer readable program code configured to control the displacement volumes of the pump strokes of the first pump and the pump strokes of the additional pumps so that a sum of the volume contribution of the first liquid occurring during a time between consecutive initiations of the first pump strokes plus the volumes of the additional liquids contributed by the additional pumps during the time between the consecutive initiations of the pump strokes of the first pump is constant throughout a duration of the predetermined composition gradient.

* * * * *